United States Patent [19]

Bishop et al.

[11] Patent Number: 4,827,923
[45] Date of Patent: * May 9, 1989

[54] PROTECTIVE FACIAL MASK

[76] Inventors: Dolores Bishop, 377 63rd St., Oakland, Calif. 94618; Mark M. Morris, 200 Grandview Ave., San Francisco, Calif. 94114

[*] Notice: The portion of the term of this patent subsequent to Jun. 9, 2004 has been disclaimed.

[21] Appl. No.: 59,557

[22] Filed: Jun. 8, 1987

Related U.S. Application Data

[63] Continuation of Ser. No. 802,838, Nov. 27, 1985, Pat. No. 4,671,271.

[51] Int. Cl.⁴ ............................................. A61M 15/08
[52] U.S. Cl. ......................... 128/206.11; 128/207.18; 128/207.11
[58] Field of Search ...................... 128/206.11, 206.12, 128/206.13, 206.16, 206.17, 206.18, 206.19, 206.21, 206.28, 207.11, 207.13, 207.18, 136, 132 R

[56] References Cited

U.S. PATENT DOCUMENTS

| | | | |
|---|---|---|---|
| 911,476 | 2/1909 | Cheesman | 128/206.12 |
| 1,127,612 | 2/1915 | Furtaw | 128/206.28 |
| 1,224,039 | 4/1917 | Synohubyk | 128/207.11 |
| 1,362,766 | 12/1920 | McGargill | 128/206.11 |
| 2,477,706 | 8/1949 | Taylor | 128/207.13 |
| 4,216,769 | 8/1980 | Grimes | 128/207.13 |
| 4,610,247 | 9/1986 | Stroup | 128/207.13 |
| 4,657,010 | 4/1987 | Wright | 128/206.16 |

FOREIGN PATENT DOCUMENTS 971409  1/1951  France ............................ 128/207.11

Primary Examiner—Edward M. Coven
Assistant Examiner—J. P. Lacyk
Attorney, Agent, or Firm—Limbach, Limbach & Sutton

[57] ABSTRACT

A protective facial mask covering the oral and nasal cavities. It slips over the user's head and comprises a single generally cylindrical, generally tubular, piece of an expandable impervious material open at each end. Two diametrically opposed ear slots and an opening below and extending between the ear slots hold the mask in place and provide for better conformity to the user's head. A filtered breathing cannula on the interior of the mask allows air to enter the nasal cavity only.

3 Claims, 3 Drawing Sheets

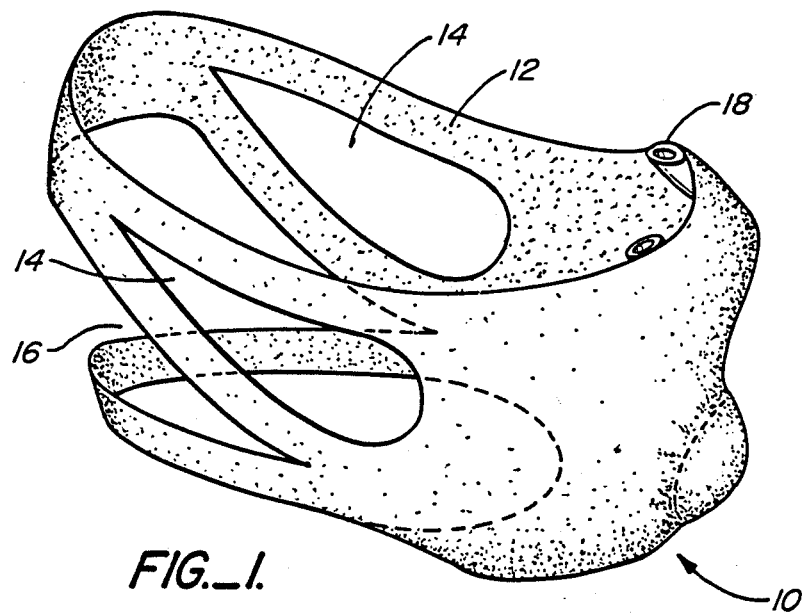
FIG._1.
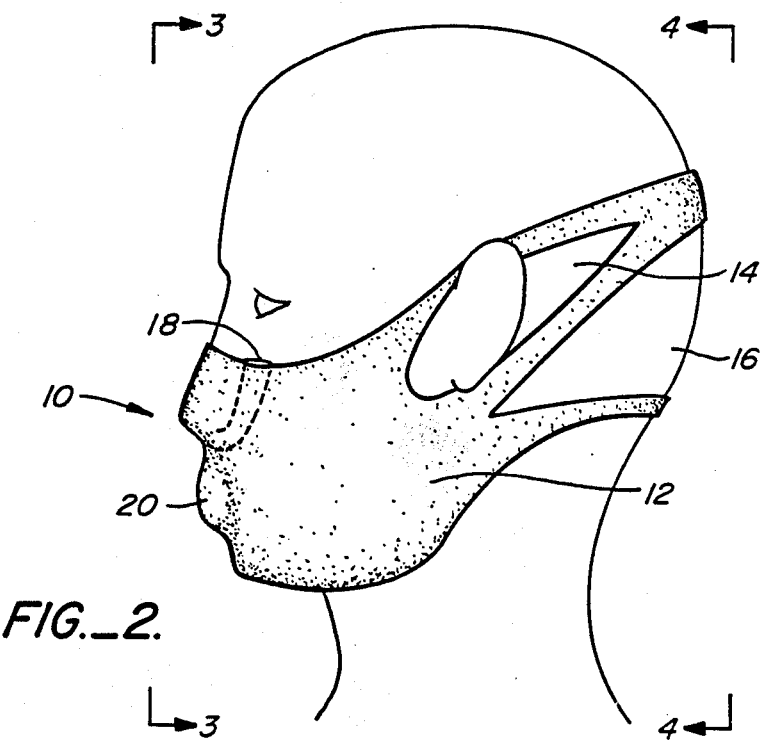
FIG._2.

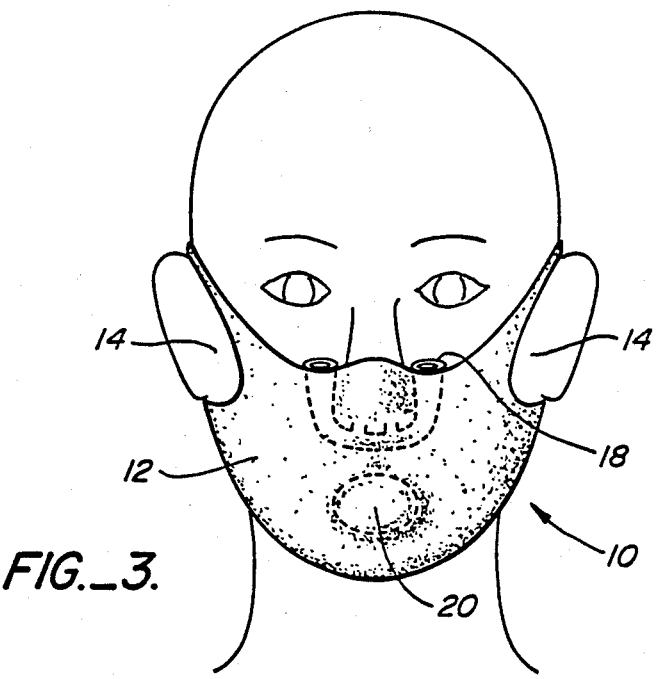
FIG._3.
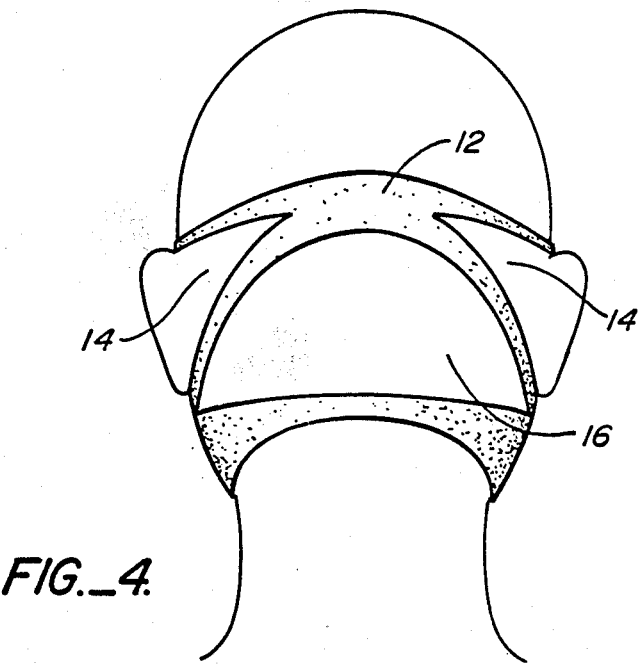
FIG._4.

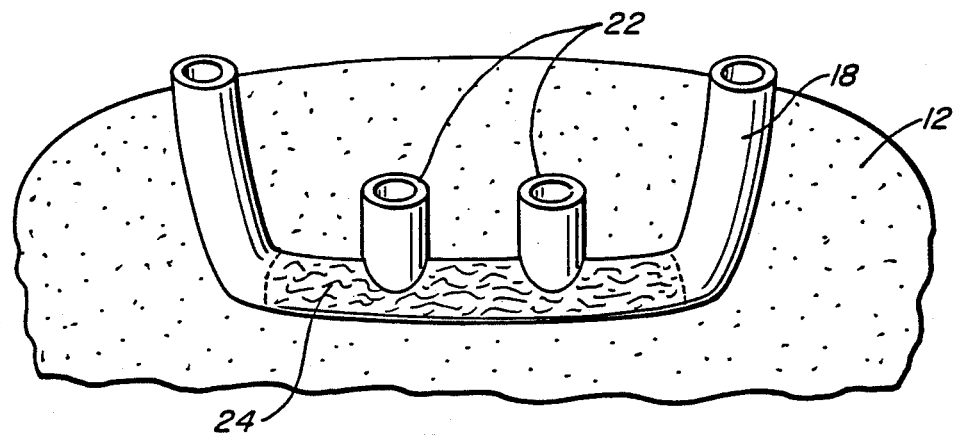
FIG._5.
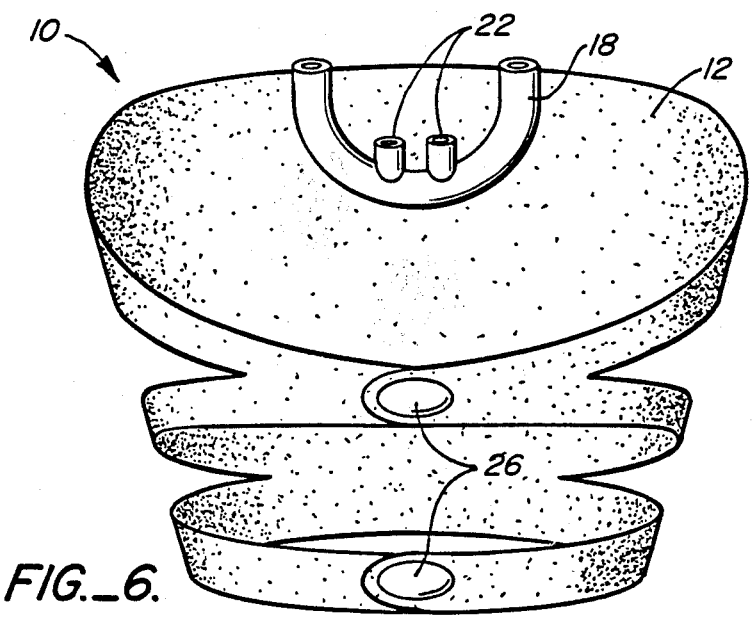
FIG._6.

PROTECTIVE FACIAL MASK

This is a continuation of application Ser. No. 802,838, filed Nov. 27, 1985, now U.S. Pat. No. 4,671,271.

FIELD OF INVENTION

This invention relates to a facial mask and more particularly to a protective facial mask which covers both the nasal and oral cavities.

BACKGROUND OF THE INVENTION

In the past there have been many attempts to provide protective facial devices for a variety of reasons. Some facial devices protected only the oral cavity, while other devices protected both the oral and nasal cavities. There are devices which protected the facial cavities from solids only, allowing liquids and air to enter into the facial cavities. Still other devices prevented solids, liquids and air from entering the nasal or oral cavity altogether.

Heretofore, the art has been without a protective facial device which covers both the oral and nasal cavities, thereby preventing liquids or solids from entering the facial cavities, while allowing air to enter the nasal cavity only. Such a protective facial device has a myriad of uses, including preventing the spread of germs, bacteria and viruses, preventing dust particles or potentially toxic sprayed liquids from entering the facial cavities and protecting the facial cavities from extreme weather conditions. Virtually anyone needing facial protection from solids, particles, sprayed liquids, liquids or air will have use for such a device.

Accordingly, it is a principal object of this invention to provide a protective facial mask which prevents solids or liquids from entering the facial cavities while allowing air to enter the nasal cavity only.

Another object of the present invention is to provide a protective facial mask which is self-adjusting and secures itself to the user's head comfortably.

Another object of the present invention is to provide a protective facial mask which filters air entering into the nasal cavity.

Still another object of the present invention is to provide a protective facial mask which can easily be put on and taken off by the user.

Yet another object of the present invention is to provide a protective facial mask that is particularly well adapted to ease and economy of manufacture.

SUMMARY OF THE INVENTION

The foregoing objects and advantages of the present invention are achieved in the embodiment illustrated herein. The present invention resides in the provision of a protective facial mask which is worn below the eyes and covers both the oral and nasal cavities. The mask slips over the user's head and comprises a single generally cylindrical, generally tubular, piece of an expandable impervious material open at each end. Two diametrically opposed ear slots and an opening below and extending between the ear slots hold the mask in place and provide for better conformity to the user's head. The impervious material is an expandable latex compound which conforms to the contours of the user's head when in place. A breathing cannula on the interior of the mask allows air to enter the nasal cavity only. This method of construction allows air to enter the nasal cavity while preventing solids or liquids from entering either the oral or nasal cavity of the user. The breathing cannula contains filtering means to preclude any foreign matter (i.e. particles) from entering the nasal cavity. A pocket-like extension lies below the cannula over the mouth of the user to facilitate speech and provide greater comfort. The mask can be comfortably worn for an extended period of time since neither breathing, hearing, speech nor sight are impaired.

The mask is of a relatively simple design and can easily be put on and taken off by the user. The mask can also be folded into a compact size for ease and economy of packaging, carrying and storage.

BRIEF DESCRIPTION OF THE DRAWING

The present invention will be more readily understandable from a consideration of the accompany drawing in which:

FIG. 1 is an isometric view of a protective facial mask of the present invention.

FIG. 2 is a side view of the mask of FIG. 1 being worn by a user.

FIG. 3 is a front view of the mask, taken along the line 3—3 of FIG. 2.

FIG. 4 is a rear view of the mask, taken along the line 4—4 of FIG. 2.

FIG. 5 is an exploded view of the breathing cannula of the mask of FIG. 1.

FIG. 6 is a rear view in perspective of another embodiment of the mask having fastening means on the back portions thereof.

DETAILED DESCRIPTION OF THE PREFERRED EMBODIMENT

In reference to the drawing, FIG. 1 is an isometric view of the protective facial mask 10 of the present invention. The mask 10 slips over a user's head and covers both the nasal and oral cavities. The mask 10 comprises a single, integral, generally cylindrical piece of an expandable impervious material 12 open at each end. The impervious material 12 may be semi-transparent to reveal the user's face. Two diametrically opposed ear slots 14 hold the generally tubular mask 10 in place on a user's head. Also, there is an opening 16 below and extending between the ear slots 14. As FIG. 1 further illustrates, a standard adult-size, surgical quality breathing cannula 18 is provided on the interior forward portion of the mask 10. The breathing cannula 18 allows air to enter the nasal cavity only.

FIG. 2 shows the mask 10 in place on a user's head. Neither liquids nor solids can enter the oral or nasal cavity while the mask is worn, yet air can enter the nasal cavity and only that. A pocket-like extension 20 lies below the breathing cannula 18 to allow the user to speak and wear the device in comfort.

FIG. 3, a front view of a user wearing the mask 10, shows that the device lies below the eyes, thereby providing for unobstructed sight. The cannula 18 precludes the mask from sliding up over the user's eyes during use. Thus, the device can be worn for an extended period of time since neither breathing, hearing, speech, nor sight are impaired.

FIG. 4, a rear view of a user wearing the device, shows how the two ear slots 14 and the opening 16 provide for good conformity to the user's head, while also holding the device in place. The breathing cannula 18, as shown in FIG. 5, provides two nostril tubes 22 that fit into each nostril of a user and allow the user to breathe freely. Filtering means 24 within the cannula 18 prevent foreign matter such as dust or sprayed liquids from entering the nasal cavity.

FIG. 6 shows another embodiment of the mask 10 with fastening means 26 on the back portions thereof. In this embodiment, the sheet of impervious material 12 is folded into tubular shape and fastened closed. The fastening means 26 can be opened for removal of the mask 10.

The protective facial mask of the present invention is quite useful as it prevents liquids and solids from entering the facial cavities while allowing air to enter the nasal cavity for breathing. The unique design of the mask provides for both comfort and stability when in use. The mask may be made of a lightweight material, easily folded for packaging, carrying and storage. The device has a variety of uses from preventing the spread of germs and bacteria to protecting workers from undesirable particles or sprayed liquids incidental to their occupations.

To those skilled in the art to which this invention relates, many changes in construction and widely differing embodiments and applications of the invention will suggest themselves without departing from the spirit and scope of the invention. This disclosures and descriptions herein are purely illustrative and are not intended to be in any sense limiting.

What is claimed is:

1. A protective facial mask covering the openings into the oral and nasal cavities comprising:

a sheet of expandable material impervious to liquids or solids to serve as a fluid barrier to the oral and nasal cavities, said sheet having sufficient flexibility to conform to the shape of the face, said sheet being dimensioned to encompass an area sufficient to cover the wearer's face from over the chin to over the nose, means mounted on said sheet serving as breathing conduits for the nasal cavities, said means extending from an upper margin of said area to a zone proximate the wearer's nostrils so as to permit nasal breathing while the facial mask is being worn, and means on said sheet for retaining the mask on the head of the wearer.

2. A protective facial mask for wearing below the eyes to cover the oral and nasal cavities comprising:

a single, one-piece generally sheet-like piece of expandable, liquid-impervious material configured to provide an upper edge for engaging a wearer's face below the eyes and above the nostrils, and providing a lower edge for engaging the wearer below the chin; said piece having retention portions thereon for encircling the head of the wearer, and means on said sheet-like material on each side of the wearer's nose serving to provide breathing passageways leading from the upper edge of said piece to the nostrils so that air enters the nasal cavity, whereby said means, the retention portions and the upper and lower edges retain the mask in position to protect the nostrils and mouth while exposing the eyes and to enable nasal breathing.

3. A facial mask for covering the oral and nasal cavities comprising: a one-piece, generally elastically expandable sheet of liquid-impervious material, an upper and a lower retention on said sheet, said retention portions serving to retain the mask in operative position on the head, said sheet providing an upper edge for engaging the wearer's face below the eyes and above the nostrils and a lower edge for engaging the wearer below the chin, and breathing cannulae secured to the interior of said sheet and leading from said upper edge on each side of the wearer's nose to a nostril engaging portion below said edge serving to permit air to enter into the nasal cavity, the two retention portions, the upper and lower edges, and the cannula retaining the mask in position to protect the nostrils and the mouth while exposing the eyes and ears and enabling nasal breathing.

* * * * *